United States Patent [19]

Fischell

[11] 4,125,116
[45] Nov. 14, 1978

[54] HUMAN TISSUE STIMULATION ELECTRODE STRUCTURE

[75] Inventor: Robert E. Fischell, Silver Spring, Md.

[73] Assignee: The Johns Hopkins University, Baltimore, Md.

[21] Appl. No.: 768,606

[22] Filed: Feb. 14, 1977

[51] Int. Cl.² .............................................. A61N 1/04
[52] U.S. Cl. .................................. 128/404; 128/419 P
[58] Field of Search ................... 128/404, 418, 419 P, 128/419 C, 419 R, DIG. 4

[56] References Cited

U.S. PATENT DOCUMENTS

| | | | |
|---|---|---|---|
| 3,543,761 | 12/1970 | Bradley | 128/418 X |
| 3,608,543 | 9/1971 | Longini | 128/DIG. 4 X |
| 3,654,933 | 4/1972 | Hagfors | 128/418 |
| 3,722,005 | 3/1973 | Cowland | 128/418 X |
| 3,724,467 | 4/1973 | Avery | 128/418 |
| 3,788,329 | 1/1974 | Friedman | 128/418 |
| 3,822,708 | 7/1974 | Zilber | 128/418 X |
| 4,010,758 | 3/1977 | Rockland et al. | 128/218 |
| 4,011,861 | 3/1977 | Enger | 128/418 X |
| 4,033,357 | 7/1977 | Helland et al. | 128/418 |

FOREIGN PATENT DOCUMENTS

| | | | |
|---|---|---|---|
| 2,604,165 | 8/1976 | Fed. Rep. of Germany | 128/419 P |
| 1,219,017 | 1/1971 | United Kingdom | 128/419 P |

Primary Examiner—Lee S. Cohen
Attorney, Agent, or Firm—Robert E. Archibald

[57] ABSTRACT

The invention generally provides an improved, implantable electrode structure for human tissue stimulation application, and particularly proposes the use of pyrolytic carbon as material from which to fabricate the stimulation electrode. For cardiac stimulation use, the proposed electrode structure can be either a bipolar or unipolar unit, wherein the distal, tip electrode is made of pyrolytic carbon and the proximal or indifferent electrode is metallic. For other tissue stimulation applications, e.g., involving the cerebellar region of the brain, the proposed electrode structure is formed of a pyrolytic carbon electrode surrounded by an outer ring electrode formed of metallic segments; the electrodes being carried on the surface of a pad of cushioning material, such as foam silicon rubber.

6 Claims, 3 Drawing Figures

HUMAN TISSUE STIMULATION ELECTRODE STRUCTURE

BACKGROUND OF THE INVENTION

In the treatment of human body malfunctions, for example, it is frequently necessary to electrically stimulate body tissue in order to produce some desirable effect. For example, and as is well-known, the human heart can be stimulated electrically to beat at a proper rate or the cerebellum can be stimulated to inhibit epileptic seizures. In such prior art tissue stimulator applications, the implantable electrode structure that interfaces between the electrical source (pulse generator) and the human tissue to be stimulated typically employ electrodes formed of pure platinum, an alloy of 90% platinum-10% iridium, and Elgiloy.

Where intended for use in an implantable human tissue stimulation unit, it is desirable and often essential that the material from which the stimulation electrode is formed possess certain characteristics. First, the electrode material must be compatible with human tissue and it should develop as little scar tissue as possible to minimize the effect of insulating the electrode surface electrically from the human tissue that is to be stimulated. Secondly, the electrode must not suffer corrosion when implanted in human tissue, nor must it electrolytically decompose when electric current flows through it. Thirdly, it is important that the electrode material have as low a polarization potential as possible so as to minimize the amount of energy dissipated at the electrode/tissue interface. Finally, the overall stimulation electrode unit should be structurally sound so that it retains its form without damage when handled by the implanting surgeon and when place in vivo.

SUMMARY OF THE INVENTION

In accordance with the present invention, a tissue stimulation electrode structure is provided wherein the negative polarity electrode is formed of pyrolytic carbon. The positive electrode, or the indifferent plate in the case of a unipolar structure, is formed of metal or metallic alloy. For cardiac stimulation employing an elongated electrode structure, such as might be implanted transvenously, the distal or tip electrode is formed of the pyrolytic carbon and operates at a negative polarity; whereas, the proximal ring (or indifferent) electrode is formed of a metal, such as platinum or metal alloy such as platinum-iridium or Elgiloy. On the other hand, when utilized to provide cerebellar stimulation, for example, the proposed electrode structure comprises a centrally disposed button electrode of pyrolytic carbon surrounded by a metallic ring electrode. The outer electrode is preferably segmented to assure that the structure will adapt more readily to an irregular tissue surface. Moreover, in one embodiment of the proposed electrode structure, the electrodes are embedded in and are exposed at one surface of a foam silicon rubber pad, which further facilitates the application of a gentle electrode or contact pressure on an irregular tissue surface.

Other objects, purposes and characteristic features of the present invention will in part be pointed out as the description of the present invention progresses and in part be obvious from the accompanying drawings wherein.

Figure 1:
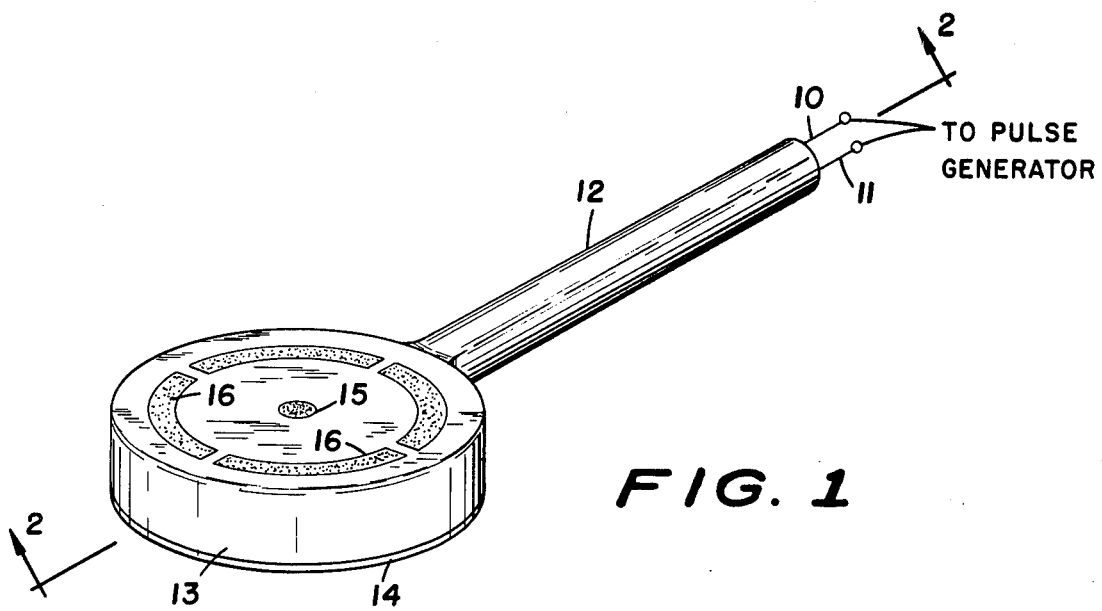
FIG. 1 is an enlarged isometric view of one embodiment of the proposed electrode structure, particularly suited for cerebellar stimulation.
Figure 2:
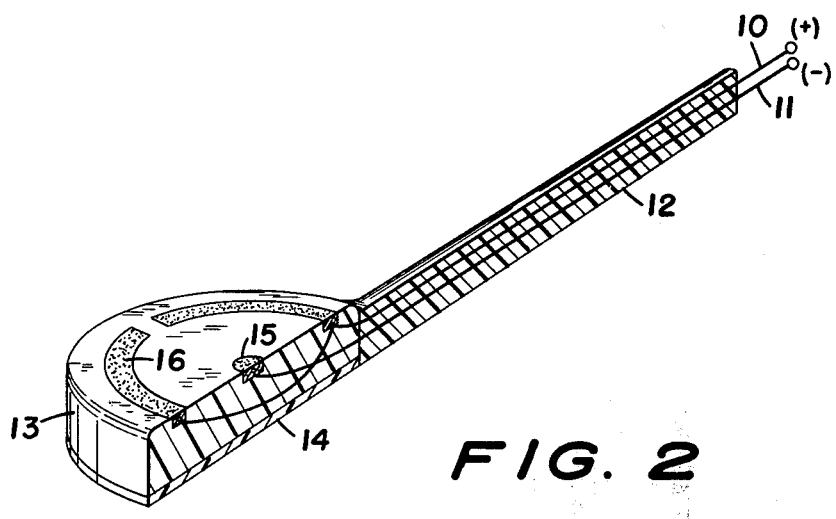
FIG. 2 is a sectional view of the electrode structure of FIG. 1 taken along line 2—2 in FIG. 1.

Referring now to FIGS. 1 and 2, the proposed electrode structure is connected to a suitable pulse generator (not shown) or other source of electrical stimulation by leads 10 and 11 which are covered by a suitable electrical insulator material 12 such as the well-known and body compatible medical Silastic. The extending left-hand end of the Silastic body 12 is bonded to a circular pad or disc of cushioning material such as foam silicon rubber 13. The bottom surface of the pad 13 is covered by a suitable backing plate 14 formed of plastic, for example.

Embedded in the opposite or upper surface of the foam rubber pad 13 is a central electrode 15 which, in accordance with the present invention, would be fabricated from pyrolytic carbon, either as a unitary pyrolytic carbon member or as pyrolytic carbon deposited on a metallic surface. Surrounding the inner electrode 15 is a series of metallic segments 16 which form a guard ring outer electrode. As shown in FIG. 2, one of the leads 11, preferably the negative polarity, is connected to the central pyrolytic carbon electrode 15; whereas, the other lead 10 (positive polarity) is connected to each of the segments 16 forming the outer ring electrode. As will be appreciated by one familiar with the field of cerebellar stimulation, it is often desirable to only stimulate from one electrode surface, e.g., the upper surface of the electrodes 15, 16 which are co-planar with the top of the foam pad 13 as shown in FIGS. 1 and 2. This conserves electric power by avoiding stray electric currents into tissue that is not to be stimulated. Moreover, the central, negative electrode 15 preferably has a small surface area and the outer electrode 16 has a relatively large surface area.

As noted above, the electrode structure shown in FIGS. 1 and 2 is particularly suited for stimulating tissue having irregular surface profile, in that the segmentation of the outer electrode 16 and embedding the electrodes 15 and 16 in a foam silicon rubber cushioning material assure that the electrodes will adapt more readily to the irregularities in the tissue surface. The cushioning pad 13 assures the application of a gentle but definite contact pressure between the electrodes and such irregular tissue surface.

As indicated above, in accordance with the present invention, there are several advantages to utilizing pyrolytic carbon for the negative central electrode 15. It has been shown to be body compatible, and unlike a metal surface it does not tend to develop scar tissue at the stimulation site. Moreover, it has been uncovered that pyrolytic carbon has a polarization potential that is less than or equal to (depending upon surface treatment) that experienced by platinum or platinum-iridium alloys and much less than the commonly used Elgiloy. Whereas pyrolytic carbon tends to electrolytically decompose when used as the source of positive pulses, it does not display this undesirable characteristic when used as the negative electrode, as here proposed.

Figure 3:
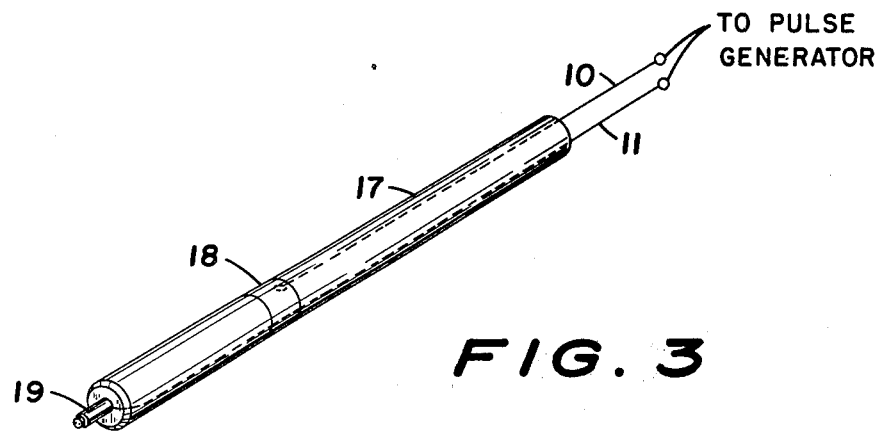
FIG. 3 is an enlarged isometric view of a second embodiment of the proposed electrode structure, particularly suited for cardiac stimulation.

FIG. 3 of the drawings illustrates a second embodiment of the present invention particularly adapted for applying stimulating pulses to a patient's heart, for cardiac pacing purposes. In this second embodiment, the overall electrode structure is formed of an elongated body 17 of suitable insulating plastic, such as the previously mentioned medical Silastic, and is configured for transvenous implantation. A proximal electrode ring 18 encircles the body 17, as generally shown in FIG. 3, and is connected preferably to the positive lead 10. The other, negative lead 11 extends through the proximal ring 18 and is connected to the distal or tip electrode 19 which is formed, in accordance with the present invention, of pyrolytic carbon.

Other modifications, adaptations and alterations of the present invention are of course possible in light of the above teachings. Within the scope of the appended claims, invention may thus be practiced otherwise than as specifically shown and described.

I claim:

1. Apparatus for applying electrical stimulation current to body tissue comprising, in combination,
    a stimulation source having a first relatively positive polarity potential and a second relatively negative polarity potential,
    an electrode structure having a first electrode means formed of pyrolytic carbon and a second metallic electrode means, and
    lead means for connecting electrically said first electrode means to the relatively negative polarity potential of said stimulation source and said second electrode means to the relatively positive polarity potential of said stimulation source.

2. The apparatus specified in claim 1 wherein said electrode structure includes an elongated member fabricated from electrically insulative and body compatible material and wherein,
    said first electrode means comprises a distal electrode affixed at the extending end of said elongated member, and
    said second metallic electrode means comprises a proximal ring electrode spaced from said distal electrode and encircling said elongated member.

3. The apparatus specified in claim 1 wherein,
    said first electrode means has a flat, substantially button configuration, and said second electrode means is in the form of a flattened ring surrounding said first electrode means,
    the exposed surfaces of said first and second electrode means lying in a common plane.

4. The apparatus specified in claim 3 wherein the second ring electrode means is formed of a plurality of segments encircling said first button electrode means.

5. The apparatus specified in claim 4 further comprising a body of cushioning material and wherein said first and second electrode means are embedded in said body of cushioning material with the exposed surfaces of said first and second electrode means substantially coplanar with a surface of said cushioning body.

6. The apparatus specified in claim 5 further including a backing plate disposed on the surface of said cushioning body opposite the surface exposing said first and second electrode means.

* * * * *